(12) United States Patent
Ahmad et al.

(10) Patent No.: US 10,962,393 B2
(45) Date of Patent: Mar. 30, 2021

(54) MULTIPHASE FLOW RATE MEASUREMENT WITH ELLIPTICAL ULTRASONIC TRANSCEIVER ARRAY

(71) Applicant: SAUDI ARABIAN OIL COMPANY, Dhahran (SA)

(72) Inventors: Talha Jamal Ahmad, Dhahran (SA); Mohamed Nabil Noui-Mehidi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 281 days.

(21) Appl. No.: 15/909,038

(22) Filed: Mar. 1, 2018

(65) Prior Publication Data
US 2019/0271576 A1  Sep. 5, 2019

(51) Int. Cl.
G01F 1/74  (2006.01)
G01F 1/66  (2006.01)
G01N 33/28  (2006.01)

(52) U.S. Cl.
CPC ............. G01F 1/663 (2013.01); G01F 1/667 (2013.01); G01F 1/74 (2013.01); G01N 33/2847 (2013.01)

(58) Field of Classification Search
CPC ............ G01F 1/663; G01F 1/667; G01F 1/74; G01N 33/2847
See application file for complete search history.

(56) References Cited

U.S. PATENT DOCUMENTS

| 7,430,924 | B2 * | 10/2008 | Gysling | G01F 1/666 |
| | | | | 73/861 |
| 9,404,781 | B2 | 8/2016 | Black et al. | |
| 9,404,890 | B2 * | 8/2016 | Sinha | G01N 29/348 |
| 9,424,671 | B1 | 8/2016 | Diverdi et al. | |
| 9,424,674 | B2 | 8/2016 | Black et al. | |
| 9,714,854 | B2 | 7/2017 | Black et al. | |
| 2008/0156107 | A1 | 7/2008 | Ao et al. | |
| 2013/0047709 | A1 * | 2/2013 | Xie | G01F 1/36 |
| | | | | 73/61.45 |
| 2013/0174669 | A1 * | 7/2013 | Sui | G01F 1/667 |
| | | | | 73/861.27 |
| 2015/0308869 | A1 * | 10/2015 | Black | G01N 29/036 |
| | | | | 73/861.04 |
| 2016/0327419 | A1 * | 11/2016 | Hellevang | G01F 1/66 |
| 2016/0341586 | A1 * | 11/2016 | Hurmuzlu | G01N 29/036 |

OTHER PUBLICATIONS

International Search Report and Written Opinion for related PCT application PCT/US2019/020268 dated May 17, 2019.

* cited by examiner

*Primary Examiner* — Gregory J Toatley, Jr.
*Assistant Examiner* — Lynda Dinh
(74) *Attorney, Agent, or Firm* — Bracewell LLP; Constance G. Rhebergen; Christopher L. Drymalla

(57) ABSTRACT

An ultrasonic transceiver array provides for measurement and determination of flow rate of oil, water and gas in a multiphase flow in a pipe or conduit. The transceiver array is mounted externally and non-invasively in an elliptical arrangement on the pipe surface, resulting in an ellipsoid section of the flow cross-sectional area to be interrogated. The single ultrasonic transceiver array forms a tomographic image of multiphase flow to determine volume fraction of each phase; measure the total flow velocity to determine flow rate of individual phases and thus provide a three phase measurement capability. Both phase fractions and flow velocities can be determined at the same time, eliminating the need for two different systems to achieve that purpose.

14 Claims, 3 Drawing Sheets

MULTIPHASE FLOW RATE MEASUREMENT WITH ELLIPTICAL ULTRASONIC TRANSCEIVER ARRAY

BACKGROUND OF THE INVENTION

1. Field of the Invention

The present invention is related to metering flow rates of a multiphase fluid in a conduit with an elliptical array of ultrasonic transceivers mounted externally about the periphery of the conduit.

2. Description of the Related Art

The simultaneous flow of two or more phases is termed multiphase flow. The flow behavior of multiphase flow is much more complex than for single phase flow and flow regime or flow pattern in a multiphase flow depends on a number of factors including the relative density ratio of one fluid to the other, difference in viscosity between fluids, and velocity (slip) of each fluid. The term fluid flow can include oil, water, gas and solid (sand). Measurement of multiphase flow parameters in hydrocarbon flow regimes and the presence of sand in flow are important in order to optimize production and to determine if sand is produced in the wellbore.

Many methods have been proposed for noninvasive measurement of multiphase flow parameters. These parameters include flow regime, flow rate, presence of solid content, volume and mass ratio of individual phases.

Non-invasive methods which utilized acoustic emission to identify various flow regimes and presence of solid content employed various parameters from flow acoustic data such as signal amplitude, rms (root mean square) value, energy and basic frequency content in the signal, and used thresholding or template matching techniques or both. One of the challenges faced with such methods has been the presence of continuous and random background acoustic and electric noise in the system and very low signal-to-noise ratio (SNR) and stochastic nature of acoustic emission signals. Because of this, most of these methods have been unable to provide accurate measurements in practical scenarios for hydrocarbon flow regimes, especially in a downhole environment in which many interrelated factors can affect the acoustics of multiphase flow in a complex manner. Also these methods did not account for acoustic variabilities and the non-stationary nature of the acoustic emission signal.

U.S. Pat. No. 9,404,781 "Multiphase Metering with Ultrasonic Tomography and Vortex Shedding" and U.S. Pat. No. 9,424,674 "Tomographic Imaging of Multiphase Flows", commonly owned with the present application, and which name inventors of the present application as inventors, provided for measurement of flow rate of a multiphase fluid within a conduit. These systems only performed multiphase fraction measurement for each phase and did not include the total volumetric flow rate measurement. Doppler frequency shift changes in the frequency of ultrasonic pulses travelling between diametrically opposed transceivers were measured and processed in determining flow velocity of the multiphase fluid. However, the determination of flow velocity of the fluid required knowledge of the velocity of the ultrasonic energy through the multiphase fluid which in turn was based on an estimate of the relative presence of the various component fluids of the multiphase fluids in the conduit.

SUMMARY OF THE INVENTION

Briefly, the present invention provides a new and improved apparatus for determining flow velocity of a multiphase fluid mixture flowing longitudinally through a conduit along with the fluid fractions. The apparatus includes an array of a plurality of transceivers mounted about peripheral external locations on the conduit. Each of the plurality of transceivers is mounted at a diametrically opposite position on the conduit from another of the plurality of transceivers to form a diametric transceiver pair. The array of the plurality of transceivers is further mounted on the conduit in a plane extending at an acute angle extending transversely to the longitudinal flow of the multiphase fluid mixture through the conduit.

The diametric transceiver pairs selectively emit ultrasonic energy to travel in each direction between the transceivers through the multiphase fluid mixture in the conduit. A processing electronics circuit forms measures of travel times of the ultrasonic energy in each direction through the multiphase fluid mixture in the conduit between the transceivers of at least one of the diametric transceiver pair. A data processing system determines flow velocity of the multiphase fluid mixture flowing longitudinally through a conduit by determining velocity of travel of the ultrasonic energy through the multiphase fluid mixture in the conduit from the determined travel times of the ultrasonic energy in each direction between the transceivers of the diametric transceiver pairs.

The data processing system further determines flow velocity of the multiphase fluid mixture flowing through the conduit from angle of the plane of mounting the array of the plurality of transceivers on the conduit, and from the determined velocity of travel of the ultrasonic energy through the multiphase fluid mixture in the conduit.

The present invention also provides a new and improved method for determining flow velocity of a multiphase fluid mixture flowing longitudinally through a conduit from wavelength measurers. The apparatus includes an array of a plurality of transceivers mounted about peripheral external locations on the conduit. Each of the plurality of transceivers is mounted at a diametrically opposite position on the conduit from another of the plurality of transceivers to form a diametric transceiver pair. The array of the plurality of transceivers mounted on the conduit in a plane also extend at an acute angle extending transversely to the longitudinal flow of the multiphase fluid mixture through the conduit.

The diametric transceiver pairs of the array of the plurality of transceivers selectively emit ultrasonic energy to travel in each direction between the transceivers through the multiphase fluid mixture in the conduit. A processing electronics circuit forms measures of travel times of the ultrasonic energy in each direction through the multiphase fluid mixture in the conduit between the transceivers of at least one of the diametric transceiver pairs. The processing electronics circuit further forms measures of the wavelength of the ultrasonic energy during travel through the multiphase fluid mixture in the conduit between the transceivers of at least one of the diametric transceiver pairs.

A data processing system determines flow velocity of the travel of the ultrasonic energy through the multiphase fluid mixture in the conduit from the determined travel times of the ultrasonic energy in each direction between the transceivers of the diametric transceiver pairs. The data processing system further determines flow velocity of the multiphase fluid mixture flowing through the conduit from the wavelength of the ultrasonic energy during travel through the multiphase fluid mixture in the conduit between the transceivers of at least one of the diametric transceiver pairs, and the determined velocity of travel of the ultrasonic energy through the multiphase fluid mixture in the conduit

DETAILED DESCRIPTION OF THE PREFERRED EMBODIMENTS

Figure 1:
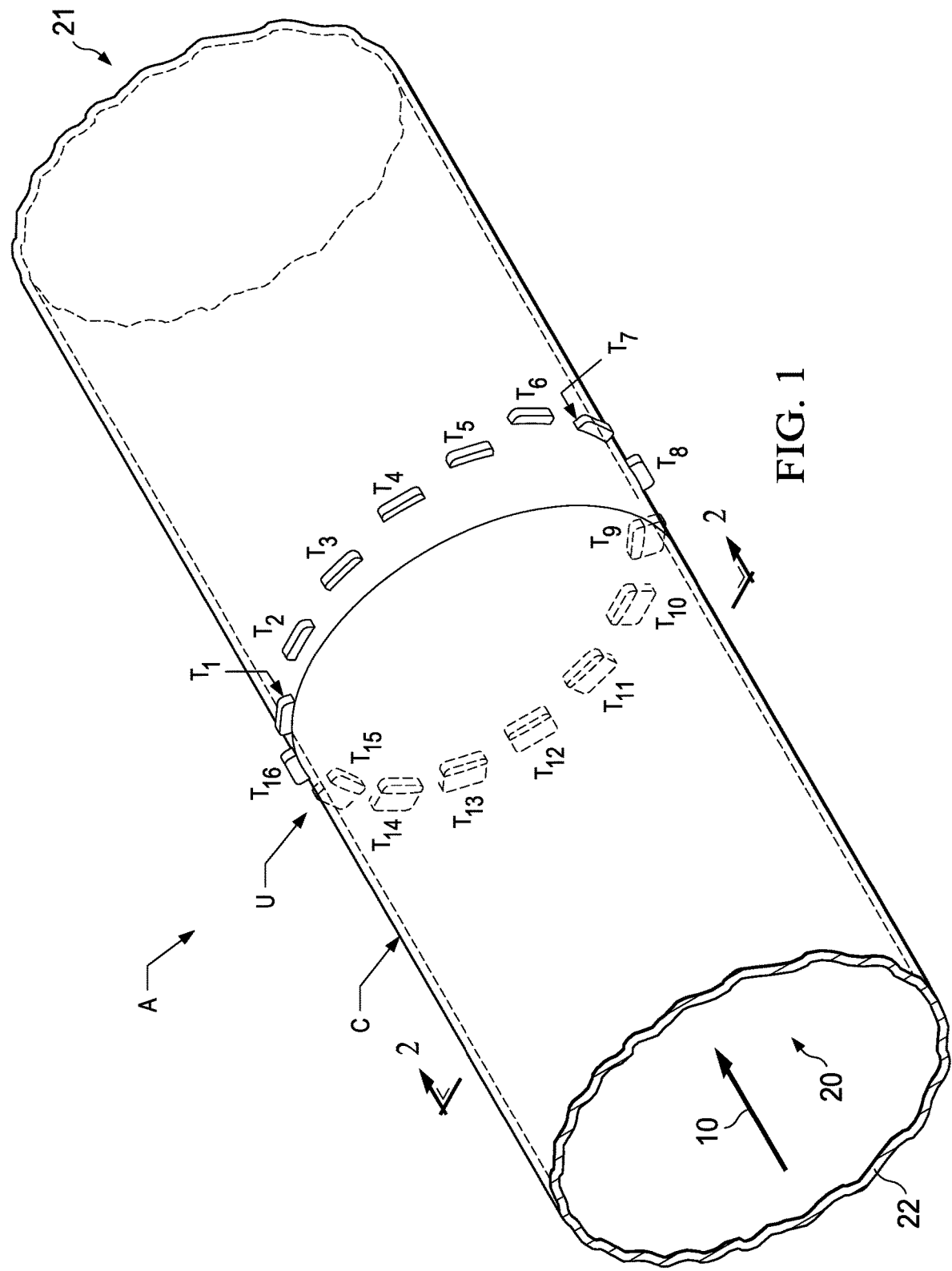
FIG. 1 is an isometric view of a multiphase flow rate measurement system with an elliptical ultrasonic transceiver array mounted on a flow conduit according to the present invention.

In the drawings, referring to FIG. 1, an apparatus A according to the present invention for determining flow velocity of a multiphase fluid mixture flowing longitudinally as indicated by an arrow 10 through a conduit C is shown. In the preferred embodiment the multiphase fluid takes the form of a three phase fluid, in which the three fluid phases are hydrocarbons, water (brine) and gas. The apparatus includes an array U of ultrasonic or ultrasound transceivers $T_1$ through $T_{16}$ which transmit ultrasonic energy to travel through the conduit C, which takes the form of a flow conduit, such as production tubing or other pipe. It should be understood that other conduits through which three phase (water (or brine), oil and gas) fluid flow velocity is to be measured may also be the subject of the present invention.

Figure 2:
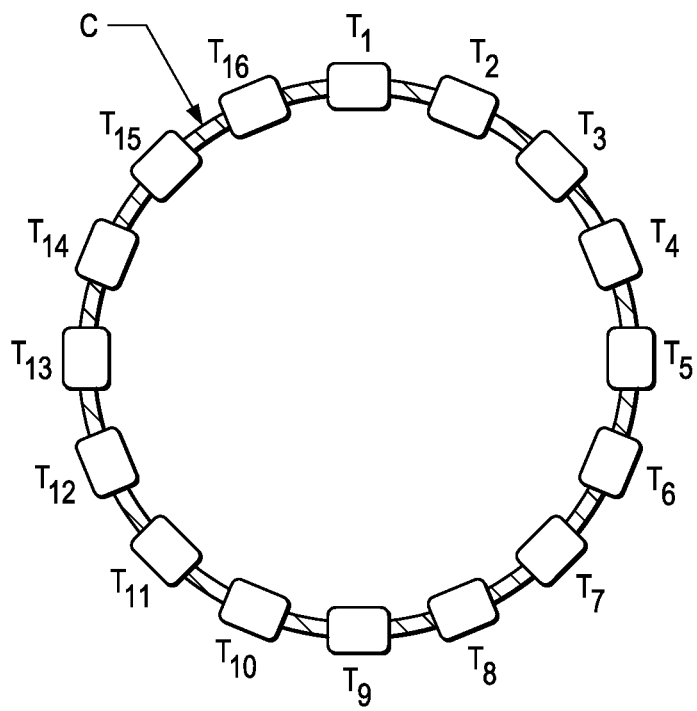
FIG. 2 is a vertical cross-sectional view taken in a plane perpendicular to a longitudinal axis of the flow conduit of FIG. 1.

Each of the plurality of transceivers $T_1$ through $T_{16}$ is mounted in a common plane as shown in FIGS. 1 and 2 at a diametrically opposite position on the conduit from another of the plurality of transceivers to form a diametric transceiver pair. Thus, transceivers $T_1$ and $T_9$ form one diametric transceiver pair, transceivers $T_2$ and $T_{10}$ form another diametric transceiver pair, and the remaining transceivers diametrically across the conduit from each other are similarly formed into diametric transceiver pairs. It should be understood that the sixteen transceivers $T_1$ through $T_{16}$ are given as an example embodiment, and that other numbers of diametrically spaced transceiver pairs may be used according to the present invention.

According to the present invention, the array U of the plurality of transceivers $T_1$ through $T_{16}$ are mounted on the conduit C in the plane at an acute angle α (FIG. 4) extending transversely to the direction indicated by arrow 10 (FIG. 1) of longitudinal flow of the multiphase fluid mixture through the conduit C. The diametric transceiver pairs of the array of the plurality of transceivers $T_1$ through $T_{16}$ selectively emit ultrasonic energy to travel in each direction between the transceivers through the multiphase fluid mixture in the conduit C. Control of the time of emission of ultrasonic energy by the individual ones of the plurality of transceivers $T_1$ through $T_{16}$ is performed, for example, according to commonly owned U.S. Pat. No. 9,424,674, "Tomographic Imaging of Multiphase Flows," which is incorporated herein by reference for all purposes.

Figure 5:
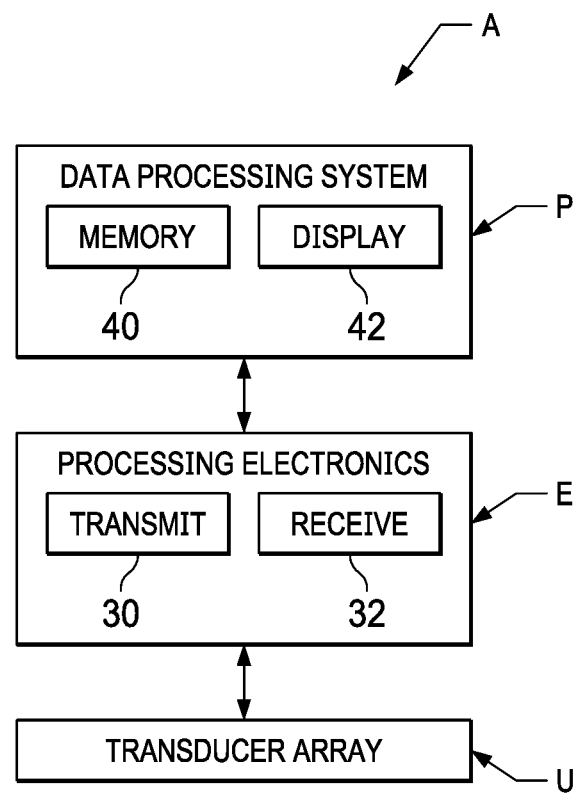
FIG. 5 is a schematic diagram of the ultrasonic travel time acquisition and processing components of the multiphase flow rate measurement system according to the present invention.

The apparatus A also includes as shown in FIG. 5 a processing electronics circuit E and a data processing system P. The processing electronics circuit E forms measures of travel times of the ultrasonic energy in each direction through the multiphase fluid mixture in the conduit C between the transceivers of at least one of the diametric transceiver pairs.

Multiphase Fluid Flow Velocity Measurement by Travel Time

FIGS. 1 and 2 show ultrasonic transceiver array U according to the present invention which measures travel times of ultrasonic energy between the diametric transceiver pairs in order to determine flow velocity of the multiphase fluid mixture in the conduit C. The multiphase fluid mixture enters as inlet multiphase flow as indicated at 10 in an inlet portion 20 through conduit or pipe C and exits as outlet flow as indicated at 21. The ultrasonic transceiver array U may be inserted or mounted, for example, according to commonly owned U.S. Pat. No. 9,404,781, "Multiphase Metering with Ultrasonic Tomography and Vortex Shedding," which is incorporated herein by reference for all purposes. If desired, the ultrasonic transceiver array U may be mounted in wall 22 of the conduit C. The transceivers $T_1$ through $T_{16}$ are mounted on the conduit C at the acute angle α extending transversely to a plane indicated at 24 (FIG. 4) which is perpendicular to the longitudinal flow as indicated at 10 (FIG. 1) of the multiphase fluid mixture.

The acute angle α relative to the plane 24 of perpendicular circular cross section of conduit C is preferably in a range of from about 10° to about 25°. The angle α should be kept to a minimum to implement, if desired, the phase fraction measurement and the tomographic imaging as described in previously mentioned U.S. Pat. No. 9,424,674, "Tomographic Imaging of Multiphase Flows."

Figure 3:
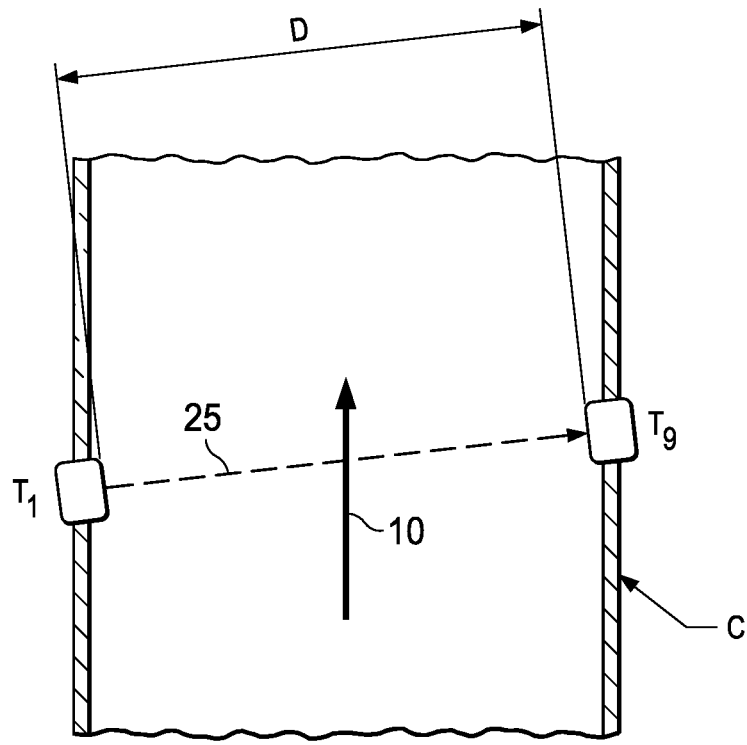
FIG. 3 is a vertical cross-sectional view taken along the longitudinal axis of the flow conduit of FIG. 1.

With the ultrasonic transceiver array U at angle α to plane 24 perpendicular to the longitudinal flow of the multiphase fluid mixture, transmitted ultrasonic signals along a travel path 25 (FIG. 3) through the multiphase fluid mixture are not perpendicular to the fluid flow, as shown at 26 in FIG. 5. The ultrasonic signal propagation between some of the diametric transceivers pairs has a component as indicated at 28 in FIG. 4 which is in-line with fluid flow. Further, ultrasonic signal propagation between some of the diametric transceivers pairs has a component against the flow direction and opposite to that indicated by arrow 28. Thus, for the diametric transceiver pairs such as $T_1$ and $T_9$; $T_2$ and $T_{10}$; and $T_3$ and $T_{11}$ which are diametrically opposite to each other on the conduit C, the ultrasonic signal transmissions have different transmission times depending on whether the signals are propagating with or against the direction 10 of the multiphase flow.

In one embodiment according to the present invention, determining the fluid flow velocity v of the multiphase fluid mixture is based on the difference Δt in transit time t of an ultrasonic signal propagating towards and against the flow direction. The time difference Δt is a measure for the average velocity of the multiphase fluid along the path of the ultrasonic signal.

Figure 4:
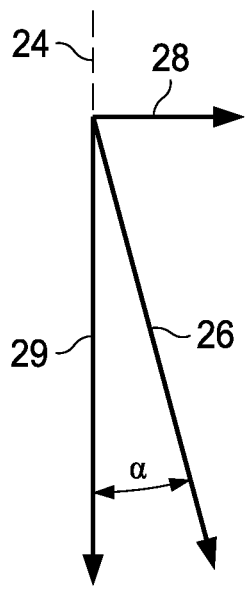
FIG. 4 is a schematic diagram of in-line and transverse components of ultrasonic wave travel through multiphase flow in the flow conduit with the elliptical ultrasonic transceiver array mounted on the flow conduit of FIG. 1.

Considering the ultrasonic transceiver pair $T_1$ and $T_9$, the transit time from transceiver $T_1$ to transceiver $T_9$ is designated $t_{1\rightarrow 9}$, and the transit time from transceiver $T_9$ to $T_1$ is designated $t_{9\to1}$. The distance between transmitting and receiving transceivers of such a transceiver pair is indicated at D in FIG. 3. Further, the angle α as shown in FIG. 4 is the acute inclination angle of the plane 24 of the ultrasonic transceiver array U with respect to the plane 24 perpendicular to the longitudinal axis of fluid flow in the conduit C. With this transceiver geometry with respect to fluid flow in the conduit C, the fluid flow velocity v of the multiphase fluid can be determined.

An ultrasonic pulse travelling with the fluid flow from transceiver $T_1$ to $T_9$ exhibits a transit time $t_{1\to9}$ of:

$$t_{1\to9} = \frac{D}{\sin\alpha} \cdot \frac{1}{(c + v \cdot \cos\alpha)} \quad (1)$$

An ultrasonic pulse travelling with the fluid flow from transceiver $T_9$ to $T_1$ exhibits a transit time $t_{9\to1}$ of:

$$t_{9\to1} = \frac{D}{\sin\alpha} \cdot \frac{1}{(c - v \cdot \cos\alpha)} \quad (2)$$

In the transit time definition relationships of Equations (1) and (2), c is the speed of sound in the multiphase fluid medium, D is the distance between transceivers T, and $T_g$, and α is the acute inclination angle of transducer array U, as described.

The time difference Δt between transit times of ultrasonic pulses between the transceivers $T_1$ and $T_9$ of that transceiver pair is:

$$\Delta t = t_{9\to1} - t_{1\to9} = v \cdot \frac{t_{9\to1} t_{1\to9} \sin 2\alpha}{D} \quad (3)$$

From this relationship, the fluid flow velocity v of the multiphase fluid mixture flowing through the conduit C is:

$$v = \frac{D}{\sin 2\alpha} \cdot \frac{t_{9\to1} - t_{1\to9}}{t_{9\to1} t_{1\to9}} \quad (4)$$

The flow rate q of the multiphase fluid mixture in the conduit C of cross-sectional area A can be determined from the fluid flow velocity v according to the following formula:

$$q = v \cdot A = v \cdot \pi \cdot \frac{S^2}{4} \quad (5)$$

$$q = \frac{\pi \cdot D^3}{4 \cdot \sin 2\alpha} \cdot \frac{t_{9\to1} - t_{1\to9}}{t_{9\to1} t_{1\to9}} \quad (6)$$

Similarly the flow rate q can be determined for other transceiver pairs, such as the transceiver pair $T_2$ and $T_{10}$, and transceiver pair $T_3$ and $T_{11}$. The flow rate can be averaged for 3 pairs, and can be averaged over time for reliable measurement.

Moreover the sound velocity c in the multiphase fluid between the transceiver pair $T_1$ and $T_9$ can be determined using the sum of transit times $t_{1\to9}$ and $t_{9\to1}$ as follows:

$$\sum T = t_{9\to1} + t_{1\to9} = \frac{2D}{c \cos\alpha} \quad (7)$$

From this relationship, the sound velocity c in the multiphase fluid between the transducer pair $T_1$ and $T_9$ can be determined:

$$c = \frac{2D}{\sin\alpha(t_{9\to1} + t_{1\to9})} \quad (8)$$

The value of sound velocity c can be determined for a number of different transceiver pairs or for each of such transceiver pairs, and can be averaged for some or all transceiver pairs to get a reliable and accurate value.

The processing electronics circuit E includes a transmit signal forming circuit or module 30 (FIG. 5) and a receive signal processing circuit or module 32. The transmit signal forming circuit 30 provides pre-amplification and a switching capability which minimizes cross talk between the different diametric transceiver pairs. The transmit signal forming circuit 30 also indicates to the data processing system D the time at which individual ones of the transmitting transceivers $T_1$ through $T_{16}$ of the diametric pairs emit their respective ultrasonic pulses. The transmit signal forming circuit 30 sends a pulse which is to be emitted as ultrasonic energy to the appropriate transceiver. The transmit signal forming circuit 30 also isolates the pulse emitting transceiver from the receive signal processing circuit 32.

The receive signal processing circuit 32 senses the arrival time at individual ones of the receiving transceivers $T_1$ through $T_{16}$ of the diametric pairs and indicates these times to the data processing system D. As has been noted, control of activation and receipt of the ultrasonic pulses may be in accordance with U.S. Pat. No. 9,424,674.

As receive signal processing circuit 32 senses the arrival time of the ultrasonic pulses after travel through the multiphase fluid from the emitting transceiver, the arrival time of the ultrasonic pulses is transferred to the data processing system D. When a tomography measurement cycle by the array U is complete, the data processing system D has received a set of measurements represent the travel times in both directions between each of the diametric transceiver pairs of transceivers $T_1$ through $T_{16}$.

As shown schematically in FIG. 4, ultrasonic pulses transmitted through the multiphase flow with a frequency f have two directional components, one as indicated at 29 at right angles to the flow and a second component as indicated at 28 either in-line with or against the flow direction 10 (FIG. 1). The addition of a flow velocity, v, results in a modification of the speed at which the ultrasonic pulses propagate through the fluid medium relative to a stationary receiving transducer. Depending on the relative sizes of the perpendicular and inline components 28 and 29, the change in velocity becomes larger or smaller. When the ultrasonic pulses propagate perpendicular to the flow, there is no change in travel time. When the ultrasonic pulses propagate in-line with the flow there is a maximum change to the travel time. When the ultrasonic pulses propagate at some angle in between in-line and perpendicular, the travel time is changed according to the sine of angle α between the perpendicular transmission plane 24, and the signal travel path between transmitter and receiver transceivers of a diametric pair.

Since the geometry of the transmitter receiver system is known, according to the present invention measured travel time difference between diametric transceiver pairs provides measures of the fluid flow velocity v of the multiphase fluid mixture, according to the physical relationships expressed in Equations (1) through (8). The measure of fluid flow velocity v of the multiphase fluid mixture so determined is then stored in memory 40 of the data processing system P, and also available as an image or printed copy on display/printer 42.

Multiphase Flow Rate Measurement by Wavelength

In another embodiment according to the present invention, determining the fluid flow velocity v of the multiphase fluid mixture is based on Doppler measurement from changes in wavelength of the ultrasonic pulses during travel through the multiphase fluid and travel times of the ultrasonic signals between diametric transceiver pairs. In the diametric transceiver pairs $T_1$ and $T_9$; $T_2$ and $T_{10}$; and $T_3$ and $T_{11}$, the flow velocity introduces a Doppler frequency shift on to the ultrasonic signal during its travel. By measuring the frequency shift between the transmitted and received ultrasonic signal, the relative flow velocity can be measured.

As noted, ultrasonic pulses transmitted with a frequency f across the multiphase flow have two components, one at right angles to the flow and a second component in-line with the flow. The addition of a flow velocity, v, results in a modification of the speed at which the ultrasonic pulses propagate through the fluid medium relative to a stationary receiving transducer. When the ultrasonic pulses propagate perpendicularly to the flow there is no change in frequency. When the ultrasonic pulses propagate in-line with the flow there is a maximum change to the frequency, and when the ultrasonic pulses propagate at some angle between perpendicular and in-line, the frequency is changed according to the size of the sine of the angle between the perpendicular transmission line, and the path between transmitter and receiver, as shown in FIG. 4. Since the geometry of the transmitter receiver system is known, according to the present invention measured wavelength (or inverse of frequency) difference of the ultrasonic pulses between diametric transceiver pairs together with measures of velocity c of the travel of ultrasonic energy in the multiphase fluid provides measures of the fluid flow velocity v of the multiphase fluid mixture.

For example, an ultrasonic signal at frequency $f_1$ (~150 KHz) is transmitted from transceiver $T_1$, which has travelled through the flow and has been received by transceiver $T_9$. The ultrasonic pulses contact the fluid particles which are flowing through the conduit C at velocity v. The wavelength $\lambda_1$ of the transmitted ultrasonic wave at frequency $f_{1\to9}$ is:

$$\lambda_1 = \frac{c}{f_{1\to9}} \qquad (9)$$

In the relationship of Equation (9), c is the speed of ultrasonic energy in the fluid which is determined using Equation (8).

As the fluid is moving with velocity v, the fluid particles moving away from the transmitting transceiver see the ultrasonic signal wavelength $\lambda_p$ as:

$$\lambda_P = \frac{c - v \cos \alpha}{f_{1\to9}} \qquad (10)$$

For the receiver transceiver, the ultrasonic signal wavelength is $\lambda_2$:

$$\lambda_2 = \frac{(c - 2 \cdot v \cos \alpha)}{f_1} = \frac{c}{f_2} \qquad (11)$$

Assuming, as is normally the case, that the fluid velocity v is considerably much less than the speed c of ultrasonic energy in the fluid, or v<<c:

$$f_2 = \frac{f_2 c}{c - 2v \cos \alpha} \qquad (12)$$

The difference $\Delta f$ in both frequencies $f_1$ and $f_2$ is thus a linear measure of the flow rate, and can be determined using the relationship below:

$$\Delta f = f_2 - f_1 = \frac{2vf_1 \cos \alpha}{c} \text{ and} \qquad (13)$$

$$v = \frac{c(f_2 - f_1)}{2f_1 \cos \alpha} \qquad (14)$$

Where v is the flow velocity of multiphase flow as indicated by arrow 10.

Phase Fraction Measurement

The phase fraction measurement for hydrocarbons, water, and gas phases can be determined using the methods provided in previously mentioned, commonly owned U.S. Pat. Nos. 9,404,781 and 9,424,674.

Even if the ultrasonic array is angled, and the area of constructed cross-sectional image of the multiphase flow is longer than the perpendicular cross section area (an elliptical image rather than a circular). Yet the ratio of the measured dispersed fraction over the whole cross section can be estimated from the inclination angle α projected over the true vertical pipe cross section.

The present invention uses a single ultrasonic transceiver array U to measure the total flow velocity to determine flow rate of individual phases. The ultrasonic array U also provides measures for forming tomographic images of multiphase flow and also volume fraction of each phase according to previously mentioned U.S. Pat. No. 9,424,674, thus providing three phase measurement capability.

With the present invention, both phase fractions and flow velocities can be determined at the same time, eliminating the need for two different systems that conventionally might be used to achieve the same purpose.

The invention has been sufficiently described so that a person with average knowledge in the field of reservoir modeling and simulation may reproduce and obtain the results mentioned herein described for the invention. Nonetheless, any skilled person in the field of technique, subject of the invention herein, may carry out modifications not described in the request herein, to apply these modifications to a determined structure and methodology, or in the use and practice thereof, requires the claimed matter in the following claims; such structures and processes shall be covered within the scope of the invention.

It should be noted and understood that there can be improvements and modifications made of the present invention described in detail herein without departing from the spirit or scope of the invention as set forth in the accompanying claims.

What is claimed is:

1. An apparatus for improved determination of flow velocity of a multiphase fluid mixture flowing longitudinally through a conduit using measures of travel times of ultrasonic energy through the multiphase fluid mixture in the conduit, comprising:
   (a) an array of a plurality of transceivers mounted about peripheral external locations on the conduit;
   (b) each of the plurality of transceivers being mounted at a diametrically opposite position on the conduit from another of the plurality of transceivers to form a diametric transceiver pair;
   (c) the array of the plurality of transceivers being mounted on the conduit in a plane extending at an acute angle ($\alpha$) extending transversely to the longitudinal flow of the multiphase fluid mixture through the conduit;
   (d) the diametric transceiver pairs of the array of the plurality of transceivers selectively emitting ultrasonic energy to travel in each direction between the transceivers through the multiphase fluid mixture in the conduit;
   (e) a processing electronics circuit configured to:
      determine, based on the ultrasonic energy selectively emitted, measures of travel times of the ultrasonic energy in each direction through the multiphase fluid mixture in the conduit between the transceivers of at least one of the diametric transceiver pairs; and
      for each of the diametric transceiver pairs:
         determine, based on the determined measures of travel times of the ultrasonic energy in each direction through the multiphase fluid mixture, sound velocity (c) of the ultrasonic energy in the multiphase fluid according to the following equation:

$$c = \frac{2D}{\sin a (t_{B \to A} + t_{A \to B})},$$

where $t_{B \to A}$ is the measure of transit time from a first transceiver of the diametric transceiver pair to a second transceiver of the diametric transceiver pair, $t_{A \to B}$ is the measure of transit time from the first transceiver of the diametric transceiver pair to the second transceiver of the diametric transceiver pair, and D is the distance between the first transceiver and the second transceiver of the diametric transceiver pair; and determine, based on the sound velocity (c) determined, the flow velocity (v) of the multiphase fluid mixture flowing longitudinally through the conduit according to the following equation:

$$v = \frac{D}{\sin 2a} \cdot \frac{t_{B \to A} - t_{A \to B}}{t_{B \to A} t_{A \to B}}.$$

2. The apparatus of claim 1, wherein the processing electronics circuit forms measures of travel times of the ultrasonic energy in each direction through the multiphase fluid mixture in the conduit between the transceivers of a plurality of the diametric transceiver pairs.

3. The apparatus of claim 1, wherein the processing electronics circuit forms measures of travel times of the ultrasonic energy in each direction through the multiphase fluid mixture in the conduit between the transceivers of each of the diametric transceiver pairs.

4. The apparatus of claim 1, wherein the data processing system includes an output display forming a display of the determined flow velocity of the multiphase fluid mixture flowing through the conduit.

5. The apparatus of claim 1, wherein the data processing system includes a memory storing a record of the determined flow velocity of the multiphase fluid mixture flowing through the conduit.

6. The apparatus of claim 1, wherein the multiphase fluid comprises a three fluid phases.

7. The apparatus of claim 1, wherein the three fluid phases comprise water, oil, and gas.

8. An apparatus for improved determination of flow velocity of a multiphase fluid mixture flowing longitudinally through a conduit using measures of wavelengths and travel times of ultrasonic energy through the multiphase fluid mixture in the conduit, comprising:
   (a) an array of a plurality of transceivers mounted about peripheral external locations on the conduit;
   (b) each of the plurality of transceivers being mounted at a diametrically opposite position on the conduit from another of the plurality of transceivers to form a diametric transceiver pair;
   (c) the array of the plurality of transceivers being mounted on the conduit in a plane extending at an acute angle ($\alpha$) extending transversely to the longitudinal flow of the multiphase fluid mixture through the conduit;
   (d) the diametric transceiver pairs of the array of the plurality of transceivers selectively emitting ultrasonic energy to travel in each direction between the transceivers through the multiphase fluid mixture in the conduit;
   (e) a processing electronics circuit configured to:
      determine, based on the ultrasonic energy selectively emitted, measures of travel times of the ultrasonic energy in each direction through the multiphase fluid mixture in the conduit between the transceivers of at least one of the diametric transceiver pairs;
      determine measures of the wavelength (A) of the ultrasonic energy in the multiphase fluid mixture in the conduit for the diametric transceiver pairs; and
      for each of the diametric transceiver pairs:
         determine, based on the determined measures of travel times of the ultrasonic energy in each direction through the multiphase fluid mixture, sound velocity (c) of the ultrasonic energy in the multiphase fluid mixture in the conduit according to the following equation:

$$c = \frac{2D}{\sin a (t_{B \to A} + t_{A \to B})},$$

where $t_{B \to A}$ is the measure of transit time from a first transceiver of the diametric transceiver pair to a second transceiver of the diametric transceiver pair, $t_{A \to B}$ is the measure of transit time from the first transceiver of the diametric transceiver pair to the second transceiver of the diametric transceiver pair, and D is the distance between the first transceiver and the second transceiver of the diametric transceiver pair; and determine, based on the sound velocity (c) determined, the flow velocity (v) of the multiphase fluid mixture flowing through the conduit according to the according to the following equations:

$$f_B = \frac{c}{\lambda_B},$$

$$f_A = \frac{c}{\lambda_A}, \text{ and}$$

$$v = \frac{c(f_B - f_A)}{2f_A \cos a},$$

where $f_A$ and $\lambda_A$ are the frequency and wavelength, respectively, of a corresponding ultrasonic signal transmitted from the first transceiver of the transceiver pair and received by the second transceiver of the transceiver pair, and $f_B$ and $\lambda_B$ are the frequency and wavelength, respectively, of a corresponding ultrasonic signal transmitted from the second transceiver of the transceiver pair and received by the first transceiver of the transceiver pair.

9. The apparatus of claim 8, wherein the processing electronics circuit forms measures of travel times of the ultrasonic energy in each direction through the multiphase fluid mixture in the conduit between the transceivers of a plurality of the diametric transceiver pairs.

10. The apparatus of claim 8, wherein the processing electronics circuit forms measures of travel times of the ultrasonic energy in each direction through the multiphase fluid mixture in the conduit between the transceivers of each of the diametric transceiver pairs.

11. The apparatus of claim 8, wherein the data processing system includes an output display forming a display of the determined flow velocity of the multiphase fluid mixture flowing through the conduit.

12. The apparatus of claim 8, wherein the data processing system includes a memory storing a record of the determined flow velocity of the multiphase fluid mixture flowing through the conduit.

13. The apparatus of claim 8, wherein the multiphase fluid comprises a three fluid phases.

14. The apparatus of claim 8, wherein the three fluid phases comprise water, oil, and gas.

* * * * *